United States Patent
Berger et al.

[11] 4,034,088
[45] July 5, 1977

[54] CEPHALOSPORIN DERIVATIVES, AND COMPOSITIONS CONTAINING THEM

[75] Inventors: Christian Berger, Le Plessis Robinson; Daniel Farge, Thiais; Georges Gros, Bourg-la-Reine; Mayer Naoum Messer, Bievres; Claude Moutonnier, Le Plessis-Robinson, all of France

[73] Assignee: Rhone-Poulenc Industries, Paris, France

[22] Filed: Apr. 30, 1975

[21] Appl. No.: 573,110

[30] Foreign Application Priority Data
May 2, 1974 France .................... 74.15226
Mar. 26, 1975 France .................... 75.09517

[52] U.S. Cl. .................... 424/246; 260/243 C
[51] Int. Cl.² ............ C07D 501/20; A61K 31/545
[58] Field of Search ............. 260/243 C; 424/246

[56] References Cited
UNITED STATES PATENTS
3,890,309  6/1975  Ochiai et al. ............... 260/243 C
3,907,787  9/1975  Teller et al. ............... 260/243 C

*Primary Examiner*—Nicholas S. Rizzo
*Attorney, Agent, or Firm*—Stevens, Davis, Miller & Mosher

[57] ABSTRACT

New cephalosporin derivatives of the general formula:

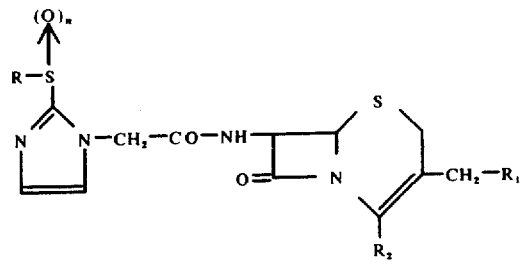

in which R represents a straight or branched chain $C_{1-4}$ alkyl radical, or a phenyl (straight or branched chain $C_{1-4}$ alkyl) radical, n is 0, 1 or 2, and either $R_1$ is a pyridinio ion and $R_2$ is a carboxylato ion, or $R_1$ represents a hydrogen atom, or an acetoxy, (5-methyl-1,3,4-thiadiazol-2-yl)-thio or (1-methyl-1,2,3,4-tetrazol-5-yl)-thio radical and $R_2$ represents a carboxy radical or a radical of the formula;

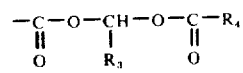

in which the radical:

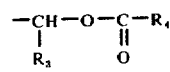

is a radical which can be removed easily by enzymatic means and in which $R_3$ represents a hydrogen atom or a straight or branched chain $C_{1-4}$ alkyl radical, a phenyl radical or a phenyl ($C_{1-2}$ alkyl) radical and $R_4$ represents a straight or branched chain $C_{1-4}$ alkyl radical, a straight or branched chain $C_{1-4}$ alkoxy radical, a cyclohexyl radical, a phenyl radical or a phenyl ($C_{1-2}$ alkyl) radical;

with the proviso that when R is an alkyl radical and either $R_1$ is a hydrogen atom or an acetoxy radical and $R_2$ is a carboxy radical or $R_1$ is a pyridinio ion and $R_2$ is a carboxylato ion, n is 1 or 2, and metal salts thereof and addition salts thereof with nitrogen-containing bases are new compounds; they possess valuable antibacterial properties, showing activity against both Gram-positive and Gram-negative bacteria.

8 Claims, No Drawings

CEPHALOSPORIN DERIVATIVES, AND COMPOSITIONS CONTAINING THEM

The present invention relates to cephalosporin derivatives, to their preparation and to compositions containing them.

The present invention provides cephalosporin derivatives of the formula:

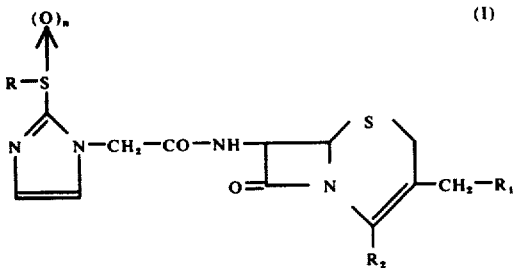

wherein
R represents a straight or branched chain $C_{1-4}$ alkyl radical or a phenyl (straight or branched chain $C_{1-4}$)alkyl radical,
n is 0, 1 or 2, and either $R_1$ is a pyridinio ion and $R_2$ is a carboxylato ion, or
$R_1$ represents a hydrogen atom or an acetoxy, (5-methyl-1,3,4-thiadiazol-2-yl)-thio or (1-methyl-1,2,3,4-tetrazol-5-yl)-thio radical, and
$R_2$ represents a carboxy radical or a radical of the formula:

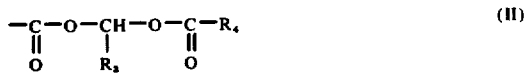

in which $R_3$ represents a hydrogen atom or a straight or branched chain $C_{1-4}$ alkyl radical, a phenyl radical or a phenyl $(C_{1-2})$alkyl radical, and $R_4$ represents a straight or branched chain $C_{1-4}$ alkyl radical, a straight or branched chain $C_{1-4}$ alkoxy radical, a cyclohexyl radical, a phenyl radical or a phenyl $(C_{1-})$ alkyl radical, the radical

contained in the radical of formula (II) being a radical which can be removed easily by enzymatic means, with the proviso that when R is an alkyl radical and either $R_1$ is a hydrogen atom or an acetoxy radical and $R_2$ is a carboxy radical or $R_1$ is a pyridinio ion and $R_2$ is a carboxylato ion, then n is 1 or 2, metal salts thereof and addition salts thereof with nitrogen-containing bases.

According to the invention, the compounds of the general formula (I) in which R, $R_1$, $R_2$ and n are as defined above can be prepared by the action of an imidazol-1-yl-acetic acid of the formula:

in which R and n are as defined above, or a reactive derivative of this acid such as an acid halide, anhydride or a mixed anhydride, on a cephalosporin of the formula:

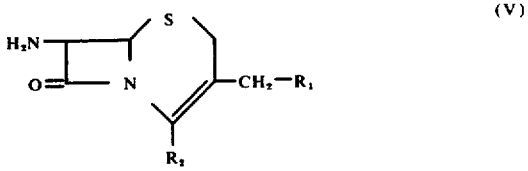

in which $R_1$ and $R_2$ are as defined above.

When an acid of formula (IV) is reacted with a cephalosporin of formula (V) in which $R_2$ represents a carboxy radical, it is preferable to protect the carboxy radical of the cephalosporin of formula (V) beforehand with a group which can be removed easily such as a tertiary butyl radical.

The reaction between the acid (IV) and cephalosporin (V) is generally carried out in an organic solvent such as dimethylformamide in the presence of a condensation agent such as dicyclohexylcarbodiimide, at a temperature of between 0 and 40° C, and then the group which protects the acid function is removed, for example by scission in an acid medium.

When the compound of formula (IV) is an acid halide, anhydride or a mixed anhydride, it is not necessary to protect the carboxy group of the cephalosporin of formula (V). In this case, the reaction is generally carried out in an organic solvent such as chloroform in the presence of an acid acceptor such as a nitrogen-containing organic base, e.g. pyridine or triethylamine, or in an aqueous-organic medium in the presence of an alkaline condensation agent such as sodium bicarbonate.

When $R_2$ represents a radical of formula (II) as defined above, the reaction is generally carried out in an organic solvent such as dimethylformamide in the presence of a condensation agent such as dicyclohexylcarbodiimide, at a temperature of between 0° and 40° C.

The cephalosporin of formula (V) in which $R_1$ represents a hydrogen atom and $R_2$ represents a carboxy radical is 7-amino-3-desacetoxy-cephalosporanic acid (7-ADCA) which can be prepared either from a penicillin, for example in accordance with the process which forms the subject of Belgian Pat. No. 747,382, or by deacetoxylation of a cephalosporin of formula (V) in which $R_1$ represents an acetoxy radical and $R_2$ is a carboxy radical, for example in accordance with the process which forms the subject of Belgian Pat. No. 779,034.

The cephalosporin of formula (V) in which $R_1$ represents an acetoxy radical and $R_2$ represents a carboxy radical is 7-amino-cephalosporanic acid (7-ACA) which can be prepared, for example, in accordance with the process which forms the subject of Belgian Pat. No. 615,955 or U.S. Pat. No. 3,239,394.

The cephalosporins of formula (V) in which $R_1$ represents a (5-methyl-1,3,4-thiadiazol-2-yl)-thio or (1-methyl-1,2,3,4-tetrazol-5-yl)-thio radical and $R_2$ represents a carboxy radical, or wherein $R_1$ represents a pyridinio ion and $R_2$ represents a carboxylato ion can be prepared by the action of 5-methyl-2-thioxo-1,3,4-thiadiazoline, 1-methyl-5-thioxo-1,2,3,4-tetrazoline or pyridine on a cephalosporin of formula (V) in which $R_1$ represents an acetoxy radical and $R_2$ represents a carboxy radical. This preparation is generally effected by heating the reactants in an alkaline aqueous medium at a temperature of between 40° and 80° C, and optionally, more particularly when $R_1$ represents a pyridinio ion, in the presence of an activator such as an alkali metal iodide or thiocyanate.

The cephalosporins of formula (V) in which $R_1$ represents a hydrogen atom or an acetoxy, (5-methyl-1,3,4-thiadiazol-2-yl)-thio or (1-methyl-1,2,3,4-tetrazol-5-yl)-thio radical and $R_2$ represents a radical of the formula (II) can be prepared from a cephalosporin of formula (V) in which $R_1$ is as defined immediately above and $R_2$ represents a carboxy radical, by any method known per se for the preparation of an ester from an acid without affecting the rest of the molecule. An alkali metal salt or a tertiary amine salt of a cephalosporin of formula (V) wherein $R_2$ represents a carboxy radical is generally reacted with a halide of formula:

  (VI)

in which $R_3$ and $R_4$ are as defined above and Y represents a halogen atom. The reaction is preferably carried out in an inert solvent such as dimethylformamide and at a temperature of between 0° and 10° C.

The imidazol-1-yl-acetic acid of formula (IV) can be prepared by saponification of the corresponding methyl or ethyl ester which can itself be prepared by the action of methyl or ethyl α-bromo- or α-chloroacetate on an imidazole derivative of the formula:

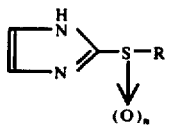  (VII)

in which R and n are as defined above.

The imidazole derivative of formula (VII) in which n is equal to zero can be prepared in accordance with the process described by W. Marckwald, Chem. Ber., 1892, 25, 2360.

The imidazole derivative of formula (VII) in which $n$ is equal to 1 or 2 can be prepared in accordance with the process which is described in U.S. Pat. No. 3,499,001.

According to a feature of the invention, the compounds of formula (I) can also be prepared by the action of an imidazole derivative of the formula (VII) on a cephalosporin derivative of the formula:

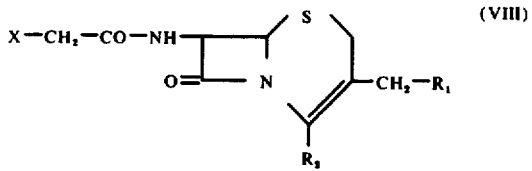  (VIII)

in which $R_1$ and $R_2$ are as defined above and X represents a halogen atom, preferably a bromine atom. This reaction is generally carried out in an organic solvent such as dimethylformamide, methylene chloride or a mixture of these solvents, at a temperature between 20° and 60° C.

When $R_2$ in the cephalosporin of formula (VIII) represents a carboxy radical, it is preferable to protect this carboxy radical before the cephalosporin is reacted, with a group which can be removed easily, for example by scission in an acid medium. An example of a suitable protecting group is the tertiary butyl radical.

The cephalosporins of formula (VIII) can be prepared by the action of an acid halide of the formula:

$$X-CH_2-CO-Y \quad (IX)$$

in which X and Y each represent a halogen atom, preferably a bromine atom, on a cephalosporin of the formula (V) for example under the conditions described in the article by L. B. Crast Jr. et. al., J. Med. Chem., 1973, 16, 1413.

According to the invention, the cephalosporins of formula (I) in which R is a straight or branched chain $C_{1-4}$ alkyl radical or a phenyl (straight or branched chain $C_{1-4}$)alkyl radical, n is 0, 1 or 2, and either $R_1$ is (i) a (5-methyl-1,3,4-thiadiazol-2-yl)-thio or (ii) a (1-methyl-1,2,3,4-tetrazol-5-yl)-thio radical and $R_2$ represents a carboxy radical, or $R_1$ is (iii) a pyridinio ion and $R_2$ is a carboxylato ion with the proviso that when R is an alkyl radical and $R_1$ is a pyridinio ion and $R_2$ is a carboxylato ion, n is 1 or 2, can be prepared by the action of (i) 5-methyl-2-thioxo-1,3,4-thiadiazoline, (ii) 1-methyl-5-thioxo-1,2,3,4-tetrazoline or (iii) pyridine respectively on a cephalosporin of the formula

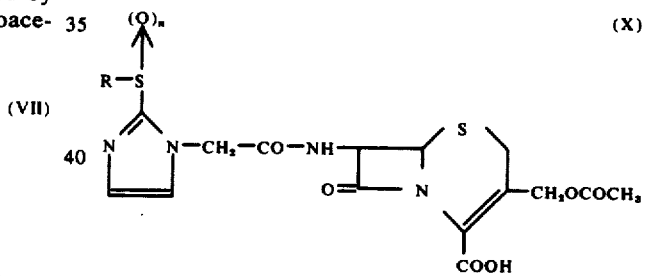  (X)

wherein R is a straight or branched $C_{1-4}$ alkyl radical or a phenyl (straight or branched $C_{1-4}$)alkyl radical and $n$ is 0, 1 or 2. In this case, the reaction is carried out under the conditions indicated above for the preparation of the cephalosporins of formula (V) in which $R_1$ represents a (5-methyl-1,3,4-thiadiazol-2-yl)-thio or (1-methyl-1,2,3,4-tetrazol-5-yl)-thio radical and $R_2$ represents a carboxy radical, or $R_1$ represents a pyridinio ion and $R_2$ represents a carboxylato ion.

The cephalosporins of formula (X) in which R is a straight or branched chain $C_{1-4}$ alkyl radical and n is 0 can be obtained by using methods described above for the preparation of cephalosporins of formula (I).

According to a further feature of the invention the cephalosporins of formula (I) in which R represents a straight or branched chain $C_{1-4}$ alkyl radical or a phenyl (straight or branched chain $C_{1-4}$)alkyl radical, n is 0, 1 or 2, $R_1$ is a hydrogen atom or an acetoxy, (5-methyl-1,3,4-thiadiazol-2-yl)-thio or (1-methyl-1,2,3,4-tetrazol-5-yl)-thio radical and $R_2$ is a radical of formula (II) can also be obtained by esterifying a cephalosporin of the formula

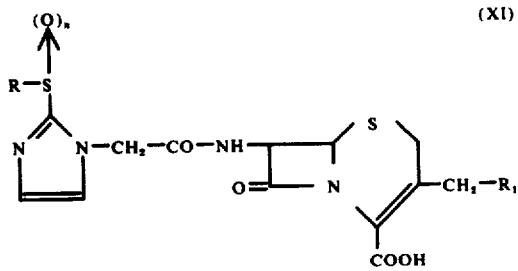

in which R, $R_1$ and n are as just defined using a method known per se for the preparation of an ester from an acid without affecting the rest of the molecule. In this case, an alkali metal salt or a tertiary amine salt of a cephalosporin of the general formula (XI) as defined above is generally reacted with a halide of formula (VI) in which $R_3$, $R_4$ and Y are as defined above. The reaction is preferably carried out in an inert solvent such as dimethylformamide, and at a temperature of between 0° and 10° C.

The cephalosporins of formula (XI) in which R is a straight or branched chain $C_{1-4}$ alkyl radical, $n$ is 0 and $R_1$ is a hydrogen atom can be obtained by using methods described above for the preparation of cephalosporins of formula (I).

The cephalosporin derivatives of formula 1 can be purified by physical methods such as chromatography or crystallisation.

The cephalosporins of formula (I) in which $R_2$ represents a carboxy radical can be converted into metal salts or addition salts of a nitrogen-containing base in accordance with known methods. These salts can be prepared by the action of an alkali metal-containing or alkaline earth metal-containing base, ammonia or an amine on a cephalosporin of formula (I) in a suitable solvent such as an alcohol, an ether, a ketone or water, or by means of an exchange reaction with a salt of an organic acid. The salt formed precipitates from solution, if necessary after concentrating the solution, and is isolated by filtration or decantation.

The cephalosporin derivatives of formula (I) possess particularly valuable antibacterial properties. They exhibit noteworthy activity in vitro and in vivo against Gram-positive and Gram-negative bacteria.

In vitro, the cephalosporins of the invention have proved active at concentrations of between 0.1 and 50 µg./cc. against staphylococcus strains which are sensitive to penicillin G (*Staphylococcus aureus* 209 P and *Staphylococcus aureus* Smith) or which are resistant to penicillin G (*Staphylococcus aureus* MB 9), and against *Escherichia coli*, Monod strain.

In vivo, the compounds of the invention have proved active against experimental infections in mice induced by *Staphylococcus aureus* Smith (sensitive to penicillin G), at doses of between 0.1 and 10 mg./kg. per day administered orally or subcutaneously; induced by *Staphylococcus aureus* MB 9 (resistant to penicillin G), at doses of between 20 and 100 mg./kg. administered subcutaneously, induced by Escherichia coli, at doses of between 1 and 50 mg./kg. per day administered subcutaneously or between 50 and 500 mg./kg. per day administered perorally, and induced by *Klebsiella pneumoniae*, at doses of between 150 and 400 mg./kg. per day administered subcutaneously.

The cephalosporins of formula (I) in which R is a methyl radical, $R_2$ is a carboxy or pivaloyloxymethoxycarbonyl radical, and either n is 1 or 2 and $R_1$ is an acetoxy, (5-methyl-1,3,4-thiadiazol-2-yl)-thio or (1-methyl-1,2,3,4-tetrazol-5-yl)-thio radical or $n$ is 0 and $R_1$ is a (5-methyl-1,3,4-thiadiazol-2-yl)-thio or (1-methyl-1,2,3,4-tetrazol-5-yl)-thio are particularly valuable. The following Examples illustrate the invention.

EXAMPLE 1

(2-Methylsulphinyl-imidazol-1-yl)-acetic acid (6 g.) is dissolved in dimethylformamide (150 cc.) and then 3-acetoxymethyl-7-amino-2-(tertiary butoxycarbonyl)-8-oxo-5-thia-1-aza-bicyclo[4,2,0]oct-2-ene (10.5 g.) and dicyclohexylcarbodiimide (6.9 g.) are added. The reagents are left in contact for 18 hours, with stirring, at a temperature of about 20° C. The precipitate formed is filtered off and the filtrate is concentrated to dryness under reduced pressure (0.1 mm.Hg). The residue is taken up in ethyl acetate (200 cc.) and the solution obtained is washed successively with water (100 cc.), a saturated solution of sodium bicarbonate (30 cc.), water (100 cc.), a solution of hydrochloric acid (0.1 N) (30 cc.) and water (100 cc.). The organic phase is dried over sodium sulphate, treated with decolorising charcoal and filtered. The filtrate is concentrated to dryness under reduced pressure (0.1 mm.Hg). A residue (8.2 g.) is obtained and is crystallised from methanol (40 cc.); after filtering off the precipitate and drying it under reduced pressure (0.1 mm.Hg), 3-acetoxymethyl-7-[(2-methylsulphinylimidazol-1-yl)-acetamido]-8-oxo-2-(tertiary butoxycarbonyl)-5-thia-1-aza-bicyclo[4,2,0]oct-2-ene (6.8 g.), which melts at 184° C., is obtained.

6.6 g. of this product are dissolved in trifluoroacetic acid (30 cc.) and kept at about 4° C., for 1 hour. The solution is then concentrated to dryness under reduced pressure (1 mm.Hg) at 20° C, the residue is taken up in acetone (100 cc.) and the solution obtained is run into isopropyl ether (200 cc.). The solid precipitate is filtered off and redissolved in methanol (750 cc.). The methanolic solution is run into isopropyl ether (2 liters). The resulting precipitate is filtered off and dried under reduced pressure (0.1 mm.Hg) to give 3-acetoxymethyl-2-carboxy-7-[(2-methylsulphinyl-imidazol-1-yl)-acetamido]-8-oxo-5-thia-1-aza-bicyclo[4,2,0]oct-2-ene (4 g.), m.p. about 220° C. with decomposition, $[\alpha]_D^{20} = +90.6° \pm 1.5°$ (c = 1, dimethylformamide).

(2-Methylsulphinyl-imidazol-1-yl)-acetic acid can be prepared in the following way:

Ethyl (2-methylsulphinyl-imidazol-1-yl)-acetate (13.1 g.) in sulphuric acid (4 N) (40 cc.) is heated under reflux for 3 hours. The sulphate ions are then removed by adding an aqueous solution of barium hydroxide and filtering off the precipitated barium sulphate. The filtrate is treated with decolorising charcoal and then concentrated to dryness under reduced pressure (20 mm.Hg). After recrystallisation from ethanol (30 cc.), (2-methylsulphinylimidazol-1yl)-acetic acid (9.4 g.), which melts at 179° C, is obtained.

Ethyl (2-methylsulphinyl-imidazol-1-yl)-acetate can be prepared in the following way:

Ethyl (2-methylthio-imidazol-1-yl)-acetate (26.4 g.) is dissolved in chloroform (250 cc.). Methachloroperbenzoic acid (26.8 g.) is added whilst keeping the temperature below 20° C, and the reagents are then left in contact for 48 hours at ambient temperature. The precipitate formed is filtered off. The filtrate is washed with a saturated solution of sodium bicarbonate (50 cc.) and then twice with water (100 cc.), dried over sodium sulphate, treated with decolorising charcoal, filtered and concentrated to dryness under reduced pressure (20 mm.Hg). An oil (27.6 g.) is obtained and is chromatographed on silica (200 g.). Elution is effected using successively ethyl acetate (1,250 cc.), a mixture of ethyl acetate and methanol (9-1 by volume) (250 cc.) and methanol (400 cc.). The eluate corresponding to the last fraction is concentrated under reduced pressure (20 mm.Hg); ethyl (2 -methylsulphinylimidazol-1-yl)-acetate (15.6 g.) is thus obtained in the form of an oil.

Ethyl (2-methylthio-imidazol-1yl)-acetate can be prepared in the following way:

Sodium hydride (4.22 g.) (50% suspension in mineral oil) is added, under a nitrogen atmosphere, to a solution of 2-methylthio-imidazole (10 g.) in dimethylformamide (100 cc.). Ethyl chloroacetate (10.8 g.) is then added and reacted for 20 hours, with stirring, at a temperature of about 20° C. The mixture is concentrated to dryness under reduced pressure (20 mm.Hg), the residue is taken up in water (1.8 liters) and the aqueous solution is extracted with methylene chloride (560 cc.). The methylene chloride extracts are washed with water, dried over sodium sulphate, treated with decolorising charcoal and concentrated to dryness under reduced pressure (20 mm.Hg) to give ethyl (2-methylthio-imidazol-1-yl)-acetate (14.5 g.) in the form of an oil.

2-Methylthio-imidazole can be prepared according to W. Marckwald, Chem. Ber., 1892, 25, 2360.

3-Acetoxymethyl-7-amino-2-(tertiary butoxycarbonyl)-8-oxo-5-thia-1-aza-bicyclo[4,2,0]oct-2-ene can be prepared according to R. J. Stedman, J. Med. Chem., 1966, 9, 444.

EXAMPLE 2

3-Acetoxymethyl-7-amino-2-(tertiary butoxycarbonyl)-8-oxo-5-thia-1-aza-bicyclo[4,2,0]oct-2-ene (5.65 g.) and dicyclohexylcarbodiimide (3.90 g.) are added to a solution of (2-mesyl-imidazol-1-yl)-acetic acid (3.53 g) in dimethylformamide (30 cc.). The reagents are left in contact for 3 days at a temperature of about 20° C, and then the solid is filtered off. The filtrate is taken up in ethyl acetate (150 cc.) and washed successively with a saturated aqueous solution of sodium bicarbonate, with 0.5 N hydrochloric acid and then with water. The organic extracts are dried over sodium sulphate and then treated with decolorising charcoal. After concentration to dryness under reduced pressure (20 mm.Hg), the crystalline residue is washed with isopropyl ether (70 cc.). 3-Acetoxymethyl-2-(tertiary butoxycarbonyl)-7-[(2-mesyl-imidazol-1-yl)-acetamido]-8-oxo-5-thia-1-aza-bicyclo[4,2,0]oct-2-ene (7.4 g.), which melts at 164° C, is thus obtained.

3-Acetoxymethyl-2-(tertiary butoxycarbonyl)-7-[(2-mesyl-imidazol-1-yl)-acetamido]-8-oxo-5-thia-1-azabicyclo[4,2,0]oct-2-ene (6 g.) is dissolved in trifluoroacetic acid (60 cc.). The reagents are contacted for 3 hours while keeping the temperature at about 4° C. The mixture is then concentrated to dryness under reduced pressure (1 mm.Hg) at 40° C, and the residue is recrystallised from acetonitrile (15 cc.) to give 3-acetoxymethyl-2-carboxy-7-[(2-mesyl-imidazol-1-yl)-acetamido]-8-oxo-5-thia-1-aza-bicyclo[4,2,0]oct-2-ene (4 g.), m.p. 223° C, $[\alpha]_D^{20} = +78.9° \pm 1.5°$ (c = 1, dimethylformamide).

(2-Mesyl-imidazol-1-yl)-acetic acid can be prepared in the following way:

Ethyl (2-mesyl-imidazol-1-yl)-acetate (21.4 g.) in 4N sulphuric acid (50 cc.) is heated under reflux for 1½ hours. A product crystallises on cooling. Crystallisation is completed by keeping the mixture in a bath of ice and water for 5 hours. After filtration, crystals (13.7 g.) which melt at 216–217° C. are obtained. Recrystallisation from water (110 cc.) gives (2-mesylimidazol-1-yl)-acetic acid (12.7 g.), melting at 218–219° C.

Ethyl (2-mesyl-imidazol-1-yl)-acetate can be prepared in the following way:

Sodium hydride (50% suspension in mineral oil) (5.04 g.) is added, under a nitrogen atmosphere, to a solution of 2-mesyl-imidazole (15.3 g.) in dimethylformamide (130 cc.). Ethyl chloroacetate (12.9 g.) is then added. Reaction is allowed to take place for 20 hours, with stirring, at a temperature of about 20° C. The reaction mixture is then poured into water (4 liters) and extraction is effected using methylene chloride (1 liter). The methylene chloride extracts are washed with water, dried over sodium sulphate, treated with decolorising charcoal and then concentrated to dryness under reduced pressure (0.5 mm.Hg) to yield ethyl (2-mesyl-imidazol-1-yl)-acetate (21.4 g.) in the form of an oil.

2-mesyl-imidazole can be prepared according to U.S. Pat. No. 3,499,001.

EXAMPLE 3

Acetone (200 cc.) is added to a solution of 7-amino-2-carboxy-3-[(1-methyl-1,2,3,4-tetrazol-5-yl)-thiomethyl]-8-oxo-5-thia-1-aza-bicyclo[4,2,0]oct-2-ene (18.4 g.) in water (110 cc.) and sodium bicarbonate (9.41 g). The mixture is cooled to about 4° C, and (2-mesyl-imidazol-1-yl)-acetyl chloride (12.4 g.) in acetone (50 cc.) is added dropwise while keeping the pH at 7 by adding a saturated aqueous solution of sodium bicarbonate. After having allowed reaction to take place for 1 hour, the acetone is removed under reduced pressure (20 mm.Hg). The pH is brought to 2.5 by adding 6 N hydrochloric acid; a solid precipitates. Ethyl acetate (100 cc.) is added, the mixture is stirred, and then the solid is filtered off and washed with ethyl acetate (500 cc.). The combined organic filtrates are dried over sodium sulphate and concentrated to dryness under reduced pressure (20 mm.Hg). A residue (8.7 g.) is obtained and is taken up in a saturated aqueous solution of sodium bicarbonate (100 cc.). The aqueous phase is washed with ethyl acetate (100 cc.) and then acidified to pH 5 by adding 6 N hydrochloric acid; a slight amount of insoluble matter is filtered off and then the filtrate is acidified to pH 2.5: a product precipitates. Extraction is effected using ethyl acetate (800 cc.), and the organic extracts are dried over sodium sulphate and concentrated to dryness under reduced pressure (20 mm.Hg). The residue is stirred with acetonitrile (40 cc.) and the solid formed is collected to yield 2-carboxy-7-[(2-mesyl-imidazol-1-yl)-acetamido]-3-[(1-methyl-1,2,3,4-tetrazol-5-yl)-thiomethyl]-8-oxo-5-thia-1-azabicyclo[4,2,0]oct-2-ene (1.08 g.), m.p. approx. 230° C, $[\alpha]_D^{20} = -42° \pm 1$ (c = 0.87, dimethylformamide).

(2-Mesyl-imidazol-1-yl)-acetyl chloride can be prepared in the following way:

Phosphorus pentachloride (22.5 g.) dissolved in methylene chloride (150 cc.) is added dropwise and whilst cooling to 5° C, to a suspension of (2-mesylimidazol-1-yl)-acetic acid (12.3 g.) in methylene chloride (50 cc.). Dimethylformamide (2 cc.) is added thereafter and the mixture is then heated under reflux for 4 hours. The mixture is cooled to 10° C, the resulting solid is filtered off and washed with methylene chloride (15 ac.) to give (2-mesyl-imidazol-1-yl)-acetyl chloride (12.4 g.), m.p. 132°–133° C.

EXAMPLE 4

3-Acetoxymethyl-2-carboxy-7-[(2-methylthioimidazol-1-yl)-acetamido]-8-oxo-5-thia-1-aza-bicyclo-[4,2,0]oct-2-ene (6.4 g.) is dissolved in a solution of sodium bicarbonate (1.26 g.) in distilled water (70 cc.). A solution of 2-methyl-5-thioxo-1,3,4-thiadiazoline (2.38 g.) and sodium bicarbonate (1.51 g.) in distilled water (150 cc.) is added. The mixture obtained is heated at 60° C, for 6 hours and is then left for 10 hours at a temperature of about 20° C. The precipitated product (1.7 g.), which melts at about 220° C, is filtered off. The pH of the filtrate is brought to 8 by adding a saturated aqueous solution of sodium bicarbonate and the aqueous phase is then washed with ethyl acetate (100 cc.). The mixture is then cooled to 4° C, and acidified to pH 4.4 by adding N hydrochloric acid. The resulting crystalline product (2.17 g.), which melts at 220° C, is filtered off.

The two batches of crystals are combined and then a saturated aqueous solution of sodium bicarbonate (160 cc.), which has been cooled beforehand to 4° C, is added. The pH is brought to 5.4 by adding a concentrated aqueous solution of citric acid. A product precipitates; precipitation is allowed to take place for 30 minutes at 4° C, and the crystals obtained are filtered off to give 2-carboxy-7-[(2-methylthio-imidazol-1-yl)-acetamido]-3-[(5-methyl-1,3,4-thiadiazol-2-yl)-thiomethyl]-8-oxo-5-thia-1-azabicyclo[4,2,0]oct-2-ene (3,13 g.), m.p. 220° C, $[\alpha]_D^{20} = -14.8° \pm 0.7°$ (c = 1, sodium bicarbonate).

2-Methyl-5-thioxo-1,3,4-thiadiazoline can be prepared according to U.S. Pat. No. 3,073,731.

The cephalosporin starting material can be prepared as follows:

(2-methylthio-imidazol-1-yl)-acetic acid (10.3 g.) is dissolved in dimethylformamide (360 cc.), by heating to 50° C. After cooling, 3-acetoxymethyl-7-amino-2-(tertiary butoxycarbonyl)-8-oxo-5-thia-1-aza-bicyclo[4,2,0]oct-2-ene (21.4 g.) and dicyclohexylcarbodiimide (13.5 g.) are added. The reagents are contacted for 18 hours, with stirring, at a temperature of about 20° C, and then the solid is filtered off. The filtrate is taken up in ethyl acetate (2.5 liters) and is washed with a saturated aqueous solution of sodium bicarbonate and then with water. Extraction is then effected using N hydrochloric acid (400 cc.), and the acid aqueous phase is washed with ethyl ether and then brought to pH 8 by adding a 4 N solution of sodium hydroxide. The oil which separates out is extracted with methylene chloride (500 cc.). The methylene chloride extracts are washed with water, dried over sodium sulphate, treated with decolorising charcoal and concentrated to dryness under reduced pressure (20 mm.Hg.). An orangeyellow oily residue (30.2 g.) is obtained and is purified by crystallisation from a mixture of methanol (32 cc.) and isopropyl ether (210 cc.) to give 3-actoxymethyl-2-(tertiary butoxycarbonyl)-7-[(2-methylthio-imidazol-1-yl)-acetamido]-8-oxo-5-thia-1-aza-bicyclo[4,2,-0]oct-2-ene (12.3 g.), m.p. 170° C.

12.3 g. of this product are dissolved in trifluoroacetic acid (100 cc.) and kept at about 4° C, for 2 hours. The solution is then concentrated to drynes under reduced pressure (1 mm.Hg) at 40° C. Benzene (40 cc.) is added and the mixture is again concentrated to dryness under reduced pressure; this step is then repeated once. The residue is taken up, with stirring, in isopropyl ether (100 cc.) and the solid product is filtered off and washed with isopropyl ether (60 cc.). Purification by recrystallisation from a mixture of acetonitrile (30 cc.) and isopropyl ether (25 cc.) gives 3-acetoxymethyl-2-carboxy-7-[(2-methylthio-imidazol-1-yl)-acetamido]-8-oxo-5-thia-1-aza-bicyclo[4,2,0]oct-2-ene (9.04 g.), m.p. 245°–247° C, $[\alpha]_D^{20} = +76.5° \pm 1.5°$ (c = 1, dimethylformamide).

(2-Methylthio-imidazol-1-yl)-acetic acid can be prepared in the following way:

Ethyl (2-methylthio-imidazol-1-yl)-acetate (14.5 g.) in 4 N sulphuric acid (30 cc.) is heated under reflux for 1 hour. The sulphate ions are then removed by adding an aqueous solution of barium hydroxide and filtering off the precipitated barium sulphate. The filtrate is treated with decolorising charcoal and is then concentrated to dryness under reduced pressure (20 mm.Hg). The residue is taken up in benzene (80 cc.) and the mixture is again concentrated to dryness under reduced pressure (20 mm.Hg); this step is then repeated. Purification of the product by recrystallisation from dimethylformamide (30 cc.) yields (2-methylthio-imidazol-1-yl)-acetic acid (7.5 g.), m.p. 176° C.

EXAMPLE 5

3-Acetoxymethyl-2-carboxy-7-[(2-methylsulphinylimidazol-1-yl)-acetamido]-8-oxo-5-thia-1-aza-bicyclo[4,2,0]-oct-2-ene (8.5 g.) and sodium bicarbonate (1.62 g.) are dissolved in water (75 cc.). A solution of 2-methyl-5-thioxo-1,3,4-thiadiazoline (2.54 g.) and sodium bicarbonate (1.62 g.) in water (75 cc.) is added and the mixture is heated at 60° C. for 6 hours. After cooling, the pH is adjusted to 6 by adding hydrochloric acid (4 N) and the mixture is washed twice with ethyl acetate (a total of 200 cc.). The mixture is acidified to pH 2 by adding hydrochloric acid (4 N); a product precipitates and is filtered off and dried under reduced pressure (1 mm.Hg) to give 7.9 g. of product. Recrystallisation from methanol (25 cc.), filtration and drying under reduced pressure (0.1 mm.Hg) gives 2-carboxy-3-[(5-methyl-1,3,4-thiadiazol-2-yl)-thiomethyl]-7-[(2-methylsulphinyl-imidazol-1-yl)-acetamido]-8-oxo-5-thia-1-aza-bicyclo[4,2,0]oct-2-ene (2.7 g.), m.p. 227° C. (with decomposition), $[\alpha]_D^{20} = -35° \pm 1°$ (c = 1, dimethylformamide).

EXAMPLE 6

3-Acetoxymethyl-2-carboxy-7-[(2-mesyl-imidazol-1-yl)-acetamido]-8-oxo-5-thia-1-aza-bicyclo[4,2,0]oct-2-ene (13.7 g.) and sodium bicarbonate (2.52 g.) are dissolved in water (140 cc.). A solution of 2-methyl-5-thioxo-1,3,4-thiadiazoline (4.75 g.) and sodium bicarbonate (3.0 g.) in water (160 cc.) is added. The mixture is heated at 60° C. for 12 hours. The mixture is allowed to cool, washed with ethyl acetate (100 cc.) and acidified to pH 2 by adding 6 N hydrochloric acid. A product precipitates and is filtered off and taken up, with stirring, in methanol (20 cc.). The solid is again filtered off and washed with methanol (40 cc.) and then with isopropyl ether (30 cc.) to give 2-carboxy-7-[(2-mesyl-imidazol-1-yl)-acetamido]-3-[(5-methyl- 1,3,4-thiadiazol-2-yl)-thiomethyl]-8-oxo-5-thia-1-aza-bicyclo-[4,2,0]oct-2-ene (6.2 g.), m.p. approximately 196° C, $[\alpha]_D^{20} = -56° \pm 2°$ (c = 1, dimethylformamide).

EXAMPLE 7

3-Acetoxymethyl-2-carboxy-7-[(2-mesyl-imidazol-1-yl)-acetamido-]-8-oxo-5-thia-1-aza-bicyclo[4,2,0]oct-2-ene (5.07 g.) and sodium bicarbonate (0.925 g.) are dissolved in water (55 cc.). The mixture is concentrated to dryness under reduced pressure (0.5 mm.Hg). Toluene (80 cc.) is added in four stages and the mixture is concentrated to dryness under reduced pressure (20 mm.Hg) in order to remove the water. The residue is taken up in dimethylformamide (30 cc.) cooled to 4° C. Chloromethyl pivalate (2.66 g.) in dimethylformamide (20 cc.) is added. After 2 hours, the mixture is concentrated to dryness under reduced pressure (0.5 mm.Hg), and the residue is taken up in ethyl acetate (300 cc.) and water (150 cc.). The organic phase is decanted and washed with a saturated aqueous solution of sodium bicarbonate (240 cc.) and then with water (300 cc.). It is dried over sodium sulphate and concentrated to dryness under reduced pressure (20 mm.Hg). A residue (3.9 g.) is obtained and is chromatographed on silica (60 g.). Elution with ethyl acetate (120 cc.) and concentration of the eluate to dryness under reduced pressure (20 mm.Hg) gives 3-acetoxymethyl-7-[(2-mesyl-imidazol-1-yl)-acetamido]-2-pivaloyloxymethoxycarbonyl-8-oxo-5-thia-1-aza-bicyclo-[4,2,0]oct-2-ene (2.9 g.) in the form of a frothy solid, $[\alpha]_D^{20} = -111.4° \pm 1.8°$ (c = 1.1, dimethylformamide); analysis:

Calculated C: 46.15, H: 4.93, N: 9.78, O: 27.94, S: 11.20%; Found C: 47.0, H: 5.4, N: 9.75, O: 28.2, S: 10.9%.

The present invention also provides pharmaceutical compositions which are useful for therapeutic purposes and which contain, as active ingredient, at least one cephalosporin of formula (I), in combination with a pharmaceutically acceptable carrier, diluent or adjuvant. These compositions can be administered orally, parenterally or rectally.

As solid compositions for oral administration it is possible to use tablets, pills, powders or granules. In these compositions, an active ingredient of the invention is mixed with one or more inert diluents or adjuvants, such as sucrose, lactose or starch. These compositions can also contain substances other than the diluents, for example a lubricant such as magnesium stearate.

As liquid compositions for oral administration, it is possible to use pharmaceutically acceptable emulsions, solutions, suspensions, syrups or elixirs containing an inert diluent such as water or liquid paraffin. These compositions can also contain substances other than the diluents, for example adjuvants such as wetting agents, sweeteners or flavouring substances.

The compositions for parenteral administration can be sterile, aqueous or non-aqueous, solutions, suspensions or emulsions. As the solvent or vehicle, it is possible to use propylene glycol, polyethylene glycol, vegetable oils, in particular olive oil, and injectable organic esters, for example ethyl oleate. These compositions can also contain adjuvants, in particular wetting agents, emulsifiers or dispersing agents. Sterilisation can be effected in various ways, for example by means of a bacteriological filter, by incorporating sterilising agents into the composition, by irradiation or by heating. These compositions can also be prepared in the form of sterile solid compositions which can be dissolved at the time of use in sterile water or any other injectable sterile medium.

The compositions for rectal administration are suppositories which can contain, in addition to the active product, excipients such as cacao butter or suppository wax.

In human therapy, the compositions according to the invention are particularly useful for the treatment of infections of bacterial origin.

The most suitable posology will normally be chosen by a doctor taking into consideration the age, weight, degree of infection and other factors characteristic of the patient to be treated. The dose for an adult patient is generally between 1 to 12 g. per day of active ingredient, administered orally, intramuscularly or intravenously.

The following Examples 8 and 9 illustrate compositions according to the invention.

EXAMPLE 8

An injectable solution having the following composition is prepared:
Sodium salt of 3-[(5-methyl-1,3,4-thiadiazol-2-yl)-thiomethyl]-2-carboxy-7-[(2-mesyl-imidazol-1-yl)-acetamido]-8-oxo-5-thia-1-aza-bicyclo[4,2,0]oct-2-ene — 260 mg.
Sodium chloride — 1.6 mg.
Injectable solution — 2 cc.

EXAMPLE 9

Tablets having the following composition are prepared in accordance with conventional techniques:
3-Acetoxymethyl-7-[(2-mesyl-imidazol-1-yl)-acetamido-]-2-pivaloyloxymethoxycarbonyl-8-oxo-5-thia-1-aza-bicyclo[4,2,0]oct-2-ene — 312 mg.
Starch — 90 mg.
Precipitated silica — 30 mg.
Magnesium stearate — 5 mg.

We claim:

1. A cephalosporin compound of the formula:

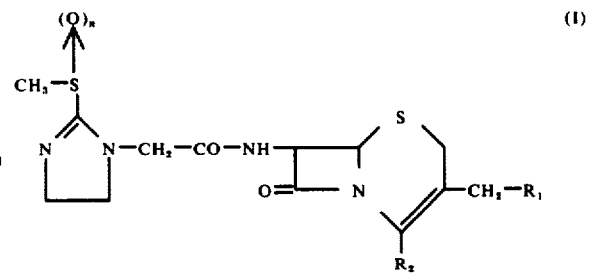

in which $R_2$ is carboxy or pivaloyloxymethoxycarbonyl and either n is 1 or 2 and $R_1$ is acetoxy, (5-methyl-1,3,4-thiadiazol-2-yl)-thio or (2-methyl-1,2,3,4-tetrazol-5-Yl)-thio, or n is 0 and $R_1$ is (5-methyl-1,3,4-thiadiazol-2-yl)-thio or (1-methyl-1,2,3,4-tetrazol-5-yl)-thio, or a pharmaceutically acceptable non-toxic metal salt thereof or an addition salt thereof with a pharmaceutically acceptable non-toxic nitrogen-containing base.

2. A cephalosporin compound as claimed in claim 1 which is 2-carboxy-7-[(2-mesyl-imidazol-1-yl)-acetamido]-3-[(1-methyl-1,2,3,4-tetrazol-5-yl)-thiomethyl]-8-oxo-5-thia-1-aza-bicyclo[4,2,0]oct-2-ene.

3. A cephalosporin compound as claimed in claim 1 which is 2-carboxy-7-[(2-methylthio-imidazol-1-yl)-acetamido]-3-[(5-methyl-1,3,4-thiadiazol-2-yl)-thiomethyl]-8-oxo-5-thia-1-aza-bicyclo[4,2,0]oct-2-ene.

4. A cephalosporin compound as claimed in claim 1 which is 2-carboxy-3-[(5-methyl-1,3,4-thiadiazol-2-yl)-thiomethyl]-7-[(2-methylsulphinyl-imidazol-1-yl)-acetamido]-8-oxo-5-thia-1-aza-bicyclo[4,2,0]oct-2-ene.

5. A cephalosporin compound as claimed in claim 1 which is 2-carboxy-7-[(2-mesyl-imidazol-1-yl)-acetamido]-3-[(5-methyl-1,3,4-thiadiazol-2-yl)-thiomethyl]-8-oxo-5-thia-1-aza-bicyclo[4,2,0]oct-2-ene.

6. A pharmaceutical antibacterial composition comprising, as active ingredient, a cephalosporin as claimed in claim 1 together with a pharmaceutically acceptable carrier, diluent or adjuvant.

7. A method of combatting bacterial infections in mammals, which comprises administering to the mammal an effective amount of a cephalosporin as claimed in claim 1 alone or together with a pharmaceutically acceptable carrier, diluent or adjuvant.

8. A cephalosporin compound as claimed in claim 1 in which $R_2$ is carboxy or a pharmaceutically acceptable non-toxic metal salt thereof or an addition salt thereof with a pharmaceutically acceptable non-toxic nitrogen-containing base.

* * * * *